US006602234B2

(12) United States Patent
Klemp et al.

(10) Patent No.: US 6,602,234 B2
(45) Date of Patent: Aug. 5, 2003

(54) DISPOSABLE ABSORBENT ARTICLE WITH CONTAINMENT STRUCTURE

(75) Inventors: Walter V. Klemp, Houston, TX (US); Paul M. Ducker, Vancouver, WA (US); Daniel D. Gardner, Jr., Petosky, MI (US); Scott W. Sneed, Friendswood, TX (US)

(73) Assignee: Associated Hygienic Products LLC, Duluth, GA (US)

( * ) Notice: Subject to any disclaimer, the term of this patent is extended or adjusted under 35 U.S.C. 154(b) by 0 days.

(21) Appl. No.: 09/502,323

(22) Filed: Feb. 11, 2000

(65) Prior Publication Data

US 2002/0151861 A1 Oct. 17, 2002

Related U.S. Application Data

(63) Continuation-in-part of application No. 09/418,902, filed on Oct. 15, 1999.

(51) Int. Cl.[7] ................................................. A61F 13/20
(52) U.S. Cl. ........................... 604/385.01; 604/385.101
(58) Field of Search ................................. 604/358, 378, 604/380, 383, 384, 385.01, 385.101, 385.16, 385.26, 385.27, 385.28

(56) References Cited

U.S. PATENT DOCUMENTS

| 4,662,877 | A |   | 5/1987  | Williams ................ 604/385 A |
| 4,738,677 | A |   | 4/1988  | Foreman ................ 604/385 R |
| 4,753,646 | A |   | 6/1988  | Enloe .................... 604/385 R |
| 4,816,025 | A |   | 3/1989  | Foreman ................ 604/385 R |
| 4,892,536 | A | * | 1/1990  | DesMarais et al. ...... 604/385.2 |
| 4,938,754 | A |   | 7/1990  | Mesek .................... 604/385.2 |
| 4,998,929 | A |   | 3/1991  | Björksund et al. ....... 604/385.2 |
| 5,019,066 | A |   | 5/1991  | Freeland et al. ......... 604/385.2 |
| 5,026,364 | A |   | 6/1991  | Robertson ............... 604/385.1 |
| 5,304,159 | A |   | 4/1994  | Tanji et al. ............. 604/385.2 |
| 5,397,318 | A |   | 3/1995  | Dreier ................... 604/385.2 |
| 5,415,649 | A |   | 5/1995  | Watanabe et al. ........ 604/385.2 |
| 5,439,459 | A |   | 8/1995  | Tanji et al. ............. 604/385.2 |
| 5,449,353 | A |   | 9/1995  | Watanabe et al. ........ 604/385.2 |
| 5,569,227 | A |   | 10/1996 | Vandemoortele et al. ... 604/382 |
| 5,672,166 | A |   | 9/1997  | Vandemoortele ......... 604/385.2 |
| 5,817,087 | A |   | 10/1998 | Takabayashi et al. ..... 604/385.2 |
| 5,827,259 | A |   | 10/1998 | Laux et al. .............. 604/385.2 |
| 5,863,288 | A | * | 1/1999  | Baker ........................ 604/378 |
| 5,931,826 | A |   | 8/1999  | Faulks et al. ............ 604/385.2 |
| 5,941,864 | A |   | 8/1999  | Roe .......................... 604/378 |
| 6,010,490 | A |   | 1/2000  | Freeland et al. ......... 604/385.1 |
| 6,017,336 | A |   | 1/2000  | Sauer ..................... 604/385.1 |
| 6,056,732 | A |   | 5/2000  | Fujioka et al. .......... 604/385.1 |
| 6,135,988 | A | * | 10/2000 | Turner et al. .............. 604/387 |

FOREIGN PATENT DOCUMENTS

| EP | 0570980 A1 |   | 5/1993 |            |
| JP | 24364      |   | 12/1987 |           |
| WO | 98/29074   | * | 7/1998 | ........... A61F/13/15 |

* cited by examiner

*Primary Examiner*—Weilun Lo
*Assistant Examiner*—Michele Kidwell
(74) *Attorney, Agent, or Firm*—Fulbright & Jaworski LLP

(57) ABSTRACT

A disposable absorbent article defined by a pair of longitudinally extending side edges and a pair of end edges extending between the side edges, has a front waist region, a back waist region, and a crotch region located between the waist regions. The disposable absorbent article also includes a topsheet, a backsheet, and an absorbent core disposed between the topsheet and the backsheet. The topsheet is provided with a plurality of openings which direct bodily exudates received into or by the crotch region to a storage space disposed below the topsheet. The topsheet is spaced generally upward from the core such that the storage space is disposed between the topsheet and the core. The disposable absorbent article further includes at least one or more elongated elastic strands which are attached to the topsheet so as to space or urge the topsheet generally upwardly from the core. Moreover, portions of the topsheet between the elastic strands are tacked down to create depressions between the strands and each of the openings are located generally in one of these depressions.

5 Claims, 6 Drawing Sheets

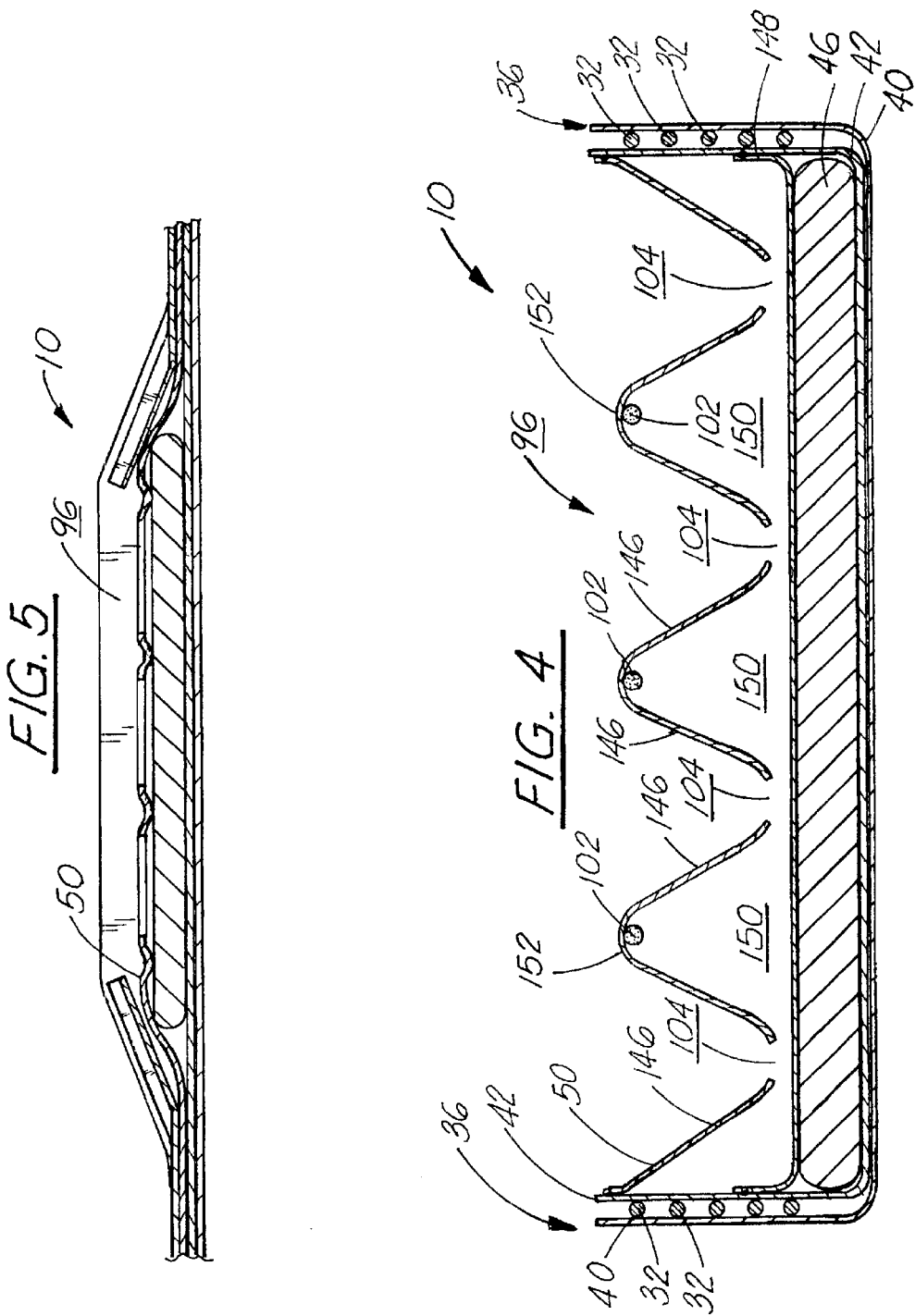

DISPOSABLE ABSORBENT ARTICLE WITH CONTAINMENT STRUCTURE

The present application is a continuation-in-part of patent application Ser. No. 09/418,902, filed Oct. 15, 1999, entitled "Disposable Absorbent With Containment Structure."

BACKGROUND OF THE INVENTION

The present invention relates generally to disposable absorbent articles such as a diaper, a training pant, or an incontinence pant.

Disposable absorbent articles are increasingly popular products. Use of disposable diapers and training pants now exceeds, by far, the use of cloth diapers. Further, advancements made in the design of disposable feminine hygiene product have produced products which offer improved comfort and utility and, thus, the use of these products have also increased. Advancements have also been made in the design of disposable adult incontinence products which are designed to control and absorb involuntarily bowel and bladder discharge associated with many medical conditions.

Disposable diapers are designed with structural features intended to enhance fit, comfort, and/or minimize leakage. In this regard, various structural designs have been developed and incorporated into diapers. For example, disposable diapers may have standing inner leg cuffs which are combined with elastic leg gatherers, such as the structures disclosed in U.S. Pat. No. 4,704,116 to Enloe, and in U.S. Pat. No. 4,695,278 to Lawson. In these structural designs, the leg cuffs and elastic leg gatherers are designed to work together so as to retain waste within a central core portion of the diaper. In another variation, a pair of "T"-shaped cuffs are disposed longitudinally on either side of the central core (see e.g., U.K. Patent Application No. 2,216,393).

These prior art designs have been effective to varying degrees in containing discharge from a wearer's body. The complexity in these structural designs also vary and may require multiple fabrication steps. For example, cuff/elastic gatherer combinations require the creation of both a cuff and an elastic gatherer which must be separately applied and which must be engineered to work together. "T"-shaped cuffs generally require additional engineering and manufacturing expense to place a "T"-shaped elasticized gasket upon a distal edge of a cuff. In an alternate design that is disclosed in U.S. Pat. No. 5,643,243 to Klemp, a diaper is provided with elasticized unitary cuffs. Each unitary cuff includes multiple strands of elastic material and provides the sole elasticizing means for containing waste within the crotch region of the diaper.

Many of these diapers and other garments are also designed with an hourglass contoured shape which improves the fit and comfort of the diaper. A disadvantage of such contoured garments is that their design generally requires the use of complex high precision machinery to form necessary intricate shapes, thereby significantly increasing the production cost associated with the garment. Moreover, many of these garments are formed from rectangular absorbent articles, typically cut in assembly line fashion from moving webs. To form a garment from such a rectangular piece of absorbent material, material is typically cut away from the longitudinal edges of the absorbent article and discarded during formation of the leg holes. While such contoured garments generally provide a more comfortable fit, these garments may be prone to leakage along the edges of the contoured region.

SUMMARY OF THE INVENTION

It is one of several features and objects of the present invention to provide an improved disposable absorbent article.

It is another feature and object of the invention to provide at least one such disposable absorbent article characterized by improved containment capabilities and/or structural features adapted to minimize leakage.

It is yet another feature and an object of the present invention to provide at least one such disposable article having a containment structure for the purpose of receiving, capturing and/or retaining body exudates.

Therefore, in accordance with one aspect of the invention, a disposable absorbent article having a front waist region, a back waist region, and a crotch region located between the waist regions is provided. The inventive disposable absorbent article includes a backsheet, an absorbent core disposed generally in the waist region and above the backsheet, and a topsheet disposed above the absorbent core. The topsheet is equipped with a plurality of openings for directing bodily exudates, which are received into or by the crotch region, to a storage space disposed below the topsheet.

In one embodiment of the invention, the topsheet is spaced generally upward from the core, such that the storage space is disposed between the topsheet and the core.

Such a storage space is adapted for storage of the generally solids portion of the bodily exudates (e.g., fecal matter). In an alternative embodiment, the disposable absorbent article employs a plurality of cores (e.g., a plurality of spaced apart elongated segmented cores) and the topsheet and the cores are arranged such that the storage space (s) is generally formed below the cores. Further, portions of the topsheet may be tacked down between these cores and each of the openings generally located between the cores.

In another aspect of the present invention, the disposable absorbent article includes a material layer (e.g., an acquisition and distribution layer) that is disposed between the storage space and the core. The material layer is adapted for receiving liquids and distributing the liquids across the core.

The inventive disposable article may further include at least one or more elongated elastic strands which are attached to the topsheet so as to space or urge the topsheet generally upwardly from the core. Portions of the topsheet located between the elastic strands may be tacked down to create depressions between the strands, and each of the openings may be located generally in one of these depressions. Each of the openings preferably has a lateral width that is substantially less than the lateral distance between the strands. Further, the topsheet may include generally inclined side walls which are directed downwardly from the ridges to the openings.

Alternatively, the disposable absorbent article is provided with a generally upstanding sidewall structure on each lateral side of the crotch region. The topsheet and the core are disposed between the sidewall structures, while the topsheet has side edges extended to and engaging the sidewall structures.

In another aspect of the invention, a disposable absorbent article is provided having a front waist region, a back waist region, and a crotch region located between the front and back waist regions. The disposable absorbent article includes a backsheet, an absorbent core disposed above the backsheet (generally in the crotch region), and a topsheet disposed above the absorbent core. The topsheet is equipped with a plurality of spaced apart elastic strands and a plurality of openings. The strands are attached to the topsheet to form a plurality of spaced apart ridges and adapted to bias the topsheet upwardly. Further, certain portions of the topsheet between the strands are tacked down (e.g., to an acquisition layer or the backsheet) to form depressions between the ridges. The openings are located between these ridges (e.g., in the depressions) and are adapted to direct bodily exudates (which are received in the crotch region) toward the core. Moreover, the topsheet may be spaced generally upward from the core to define at least one storage space therebetween. Such a storage space is particularly adapted to receive and store the solids portions of the bodily exudates.

In yet another aspect of the invention, a disposable absorbent article is provided with a pair of longitudinally extending side edges and a pair of end edges which define a front waist region, a back waist region, and a crotch region located between the front and back waist regions. The inventive disposable absorbent article includes a backsheet layer, an absorbent core disposed above the backsheet and generally in the crotch region, and a topsheet. The topsheet has a plurality of openings and is spaced generally upward from the core (e.g., by elastic strands attached to the topsheet) to define a storage space between the core and the topsheet. The disposable absorbent article further includes a containment pocket having a depth dimension. This containment pocket is disposed generally in the crotch region and is bounded by a substantially continuous containment wall that extends generally upwardly from the topsheet. The openings of the topsheet are disposed inside of the containment wall and are adapted to direct exudates received in the containment pocket (i.e., above the topsheet) into the storage space below the topsheet.

Preferably, the containment wall has two elastic end wall sections and two side intermediate wall sections. Each of the elastic end wall sections has a central portion and oppositely disposed side portions and each of the intermediate wall sections has oppositely disposed end portions. The side portions of the elastic wall sections are secured to an end portion of one of the intermediate wall sections such that the intermediate wall sections are biased generally upwardly. Further, the disposable absorbent article may include an end strip secured generally to each of the waist regions. The end strips include elastic inward sections which are spaced away from the topsheet and form the elastic wall sections of the containment wall.

Other and further objects, features, and advantages of the present invention will be apparent from the description provided herein of presently preferred embodiments of the invention, given for the purpose of disclosure, and taken in conjunction with the accompanying drawings.

BRIEF DESCRIPTION OF THE DRAWINGS

FIG. 4 is a cross-sectional view of the disposable absorbent article taken along line 4—4 in FIG. 1;

FIG. 5 is a cross-sectional view of the disposable absorbent article taken along line 5—5 in FIG. 1;

DETAILED DESCRIPTION OF THE DRAWINGS

FIGS. 1–5 depict a disposable absorbent garment or article 10 embodying the invention. The disposable absorbent article 10 is of the type which can be placed against or in proximity to the body of a wearer so as to absorb and to contain various bodily exudates. In particular, the disposable absorbent article 10 depicted in the figures and, described in more particular detail below, is in the form of a diaper 10. It should be noted, however, that the present invention is adaptable or applicable to a variety of disposable absorbent articles and garments, including training pants and a variety of adult incontinence products. Accordingly, the present invention is not intended to be limited to the diaper structures and the processes specifically described and illustrated herein. For purposes of description, the following discussion will be directed to an exemplary disposable diaper only.

In addition, the invention will be described in the context of its various configurations and aspects. It should be appreciated that alternative arrangements of the inventive disposable garment or article may comprise various combinations, which include one or more of the various configurations and aspects of the invention.

Figure 1:
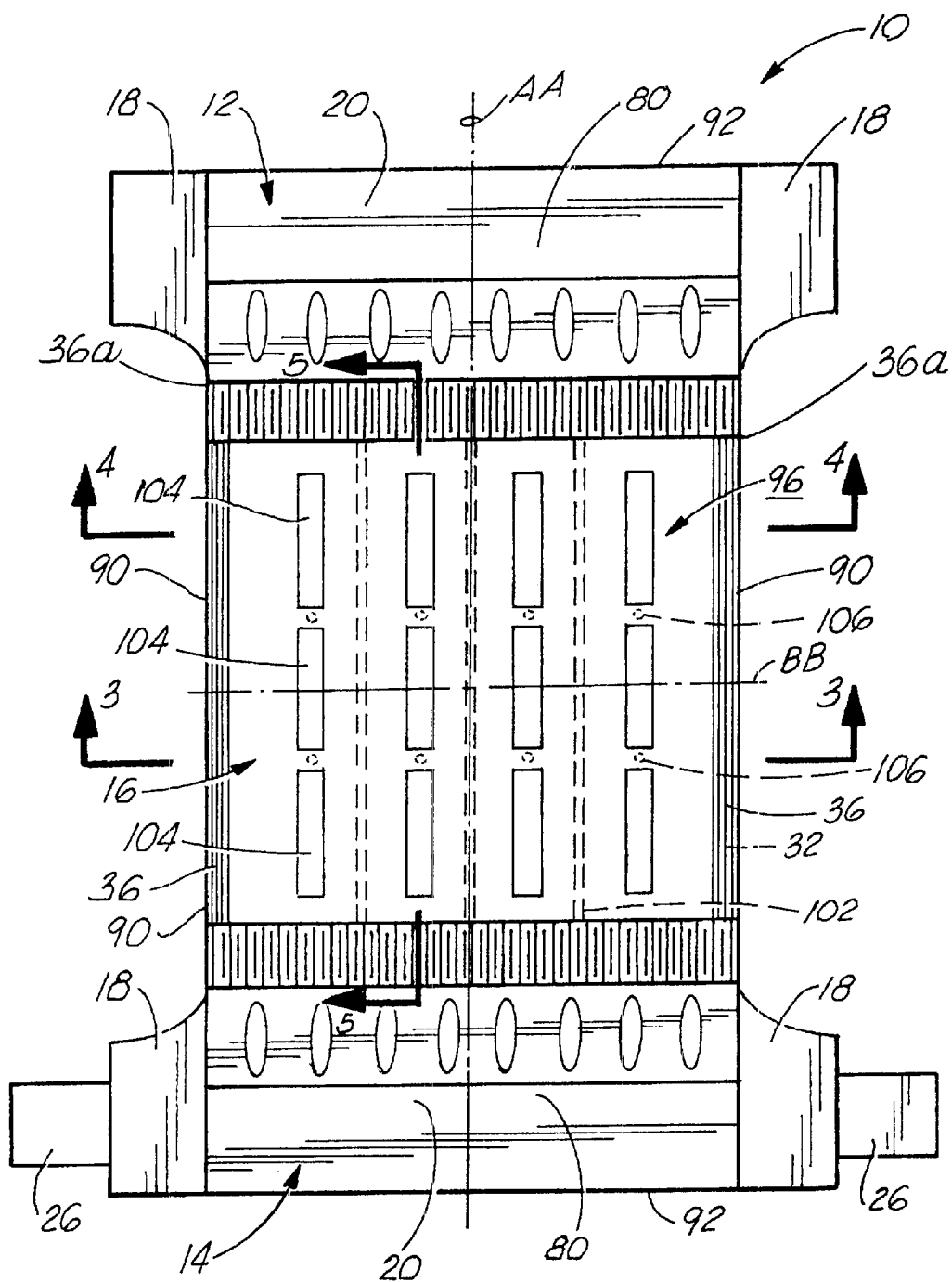
FIG. 1 is a plan view of a disposable absorbent article according to the present invention.

FIG. 1 illustrates a composite web structure of the diaper 10 in a generally flat and unfolded configuration which the diaper 10 assumes during one point in the manufacturing process (when it is stretched in the longitudinal direction). As will be explained further below, the web structure may be subsequently trimmed, folded, sealed, welded and/or otherwise manipulated to form a disposable diaper 10 in a finished or final form.

To facilitate description of the diaper 10 embodying the invention, description will refer to a longitudinally extended axis AA, a laterally extending central axis BB, a pair of longitudinally extending side edges 90, and a pair of end edges 92 which extend between side edges 90 (see FIG. 1). Along the longitudinal axis AA, the diaper 10 includes a first end region or front waist region 12, a second end region or back waist region 14, and a crotch region 16 disposed therebetween. Each of the front and back waist regions 12, 14 is characterized by a pair of ear regions or ears 18, which are located on either side of a central body portion 20 and extend laterally from the side edges 90. A fastening structure 26 (e.g., a conventional tape fastener) is affixed to each of the ears 18 along the back waist region 14 of the diaper 10.

As shown in FIG. 1, the diaper 10 is characterized by a generally hourglass shape wherein an intermediate portion of the side edges 90 (generally in the area of the crotch region 16) is biased generally upwardly (i.e., to partially form upwardly disposed longitudinal walls). When the diaper 10 is worn about the waist of the wearer, the front waist region 12 is fitted adjacent the front waist area of the wearer, the back waist region 14 is fitted adjacent the back waist area, and the crotch region 16 fits about and underneath the crotch area. To properly secure the diaper 10 to the wearer, the ears 18 of the back waist region 14 are brought around the waist of the wearer and toward the front and into alignment with the ears 18 of the front waist region 12. This securing surface may be located on or provided by the interior or exterior surface of the front waist region 12. Alternatively, the fasteners 26 may be located on the ears 18 of the front waist region 12 and made securable to the ears 18 of the back waist region 14. In one further example, a tab structure having hook structures may be attached to the ears 18 of the waist region 14 and made securable to loop members found on the front waist region 12. Such a "hook and loop" concept (and other generally known fastening structures) is generally known and practiced in the art and may be incorporated into the present invention design by one skilled in the art having access to the disclosure provided herein.

Figure 2:
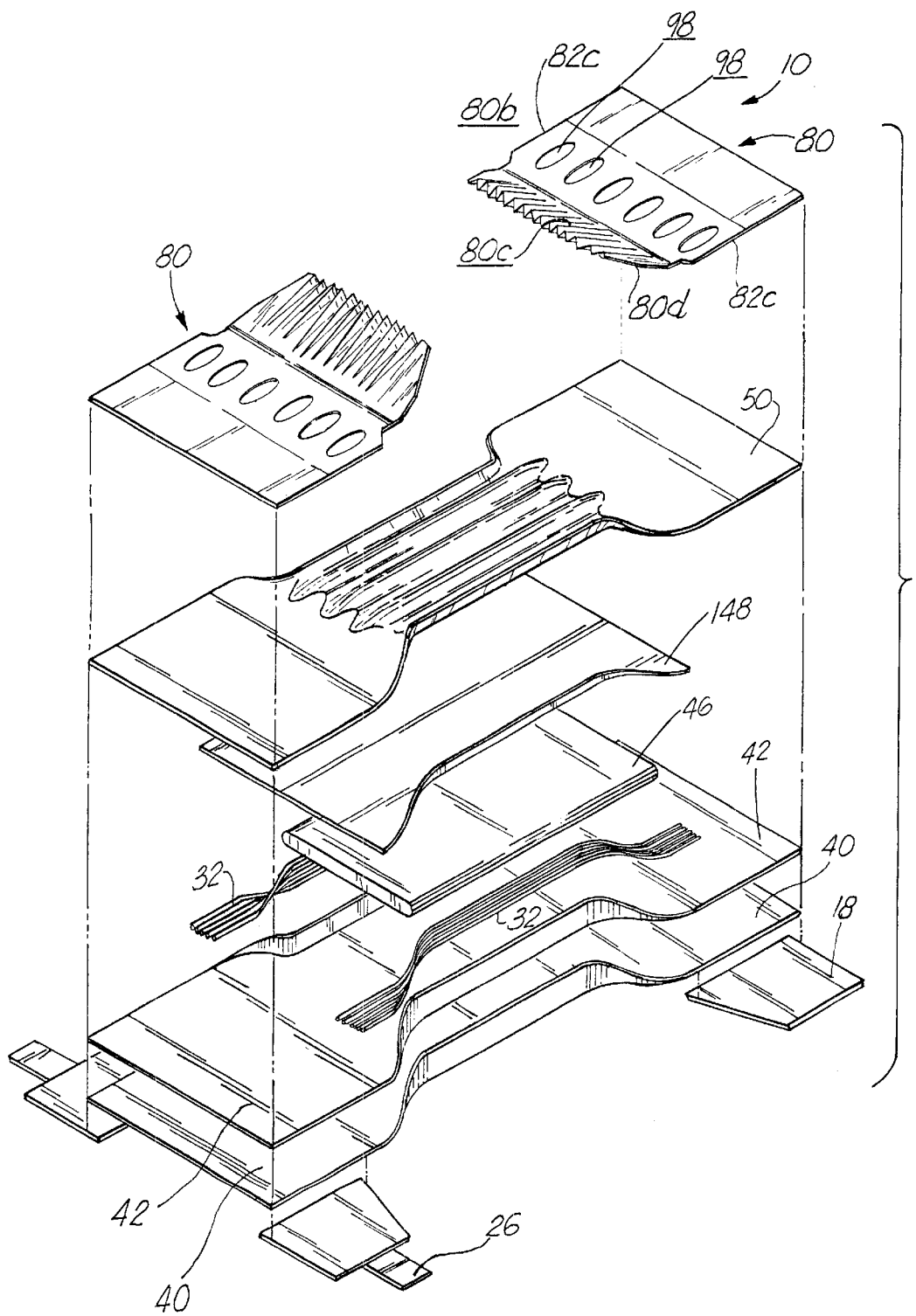
FIG. 2 is an exploded view of the disposable absorbent article of FIG. 1.

The diaper 10 of the present invention also features one or more longitudinally stretchable elastic members or leg elastics 32 positioned adjacent each of the two side edges 90 of the diaper 10 (see FIG. 2). When the diaper 10 is properly worn by the wearer, each leg elastic 32 encircles a leg of the wearer and provides a quasi-seal thereabout which substantially prevents leakage from the interior of the diaper 10. Such leg elastics 32 may be applied in the stretched or extended condition. In one application of invention, the elastics 32 are placed between a topsheet or top layer and a bottom sheet or bottom layer in the stretched condition, and, then, attached to one or both of the sheets or layers (i.e., by glue or other adhesive). When subsequently released, the elastics 32 retract and form gathered leg regions or leg gatherers 36 as it pulls adjacent material therewith (see e.g., FIGS. 1, 3 and 4).

Figure 3:
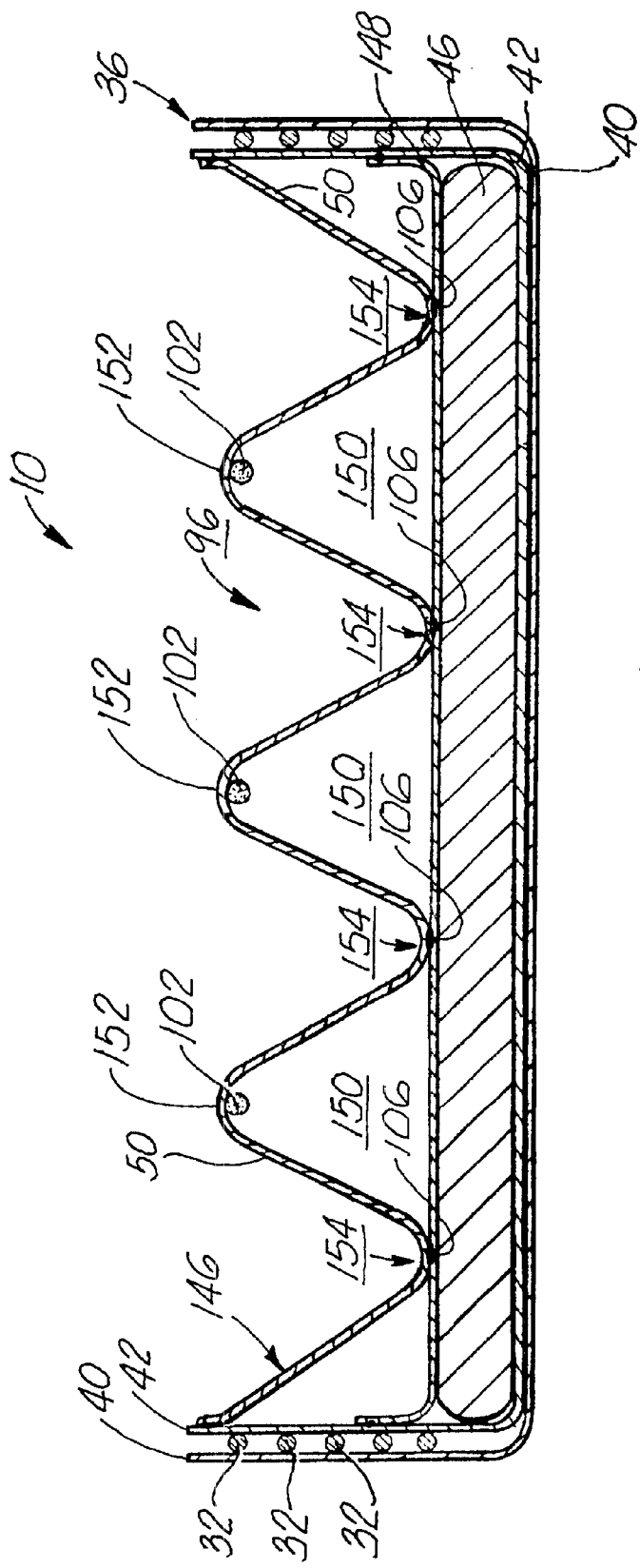
FIG. 3 is a cross-sectional view of the disposable absorbent article taken along line 3—3 in FIG. 1.

Now referring primarily to the exploded view of FIG. 2, a diaper 10 according to the invention typically features two to five layers. These five layers may include a nonwoven backsheet 40, a film barrier 42, a fluffed core 46, an acquisition layer 148, a topsheet 50, and a pair of end strips or tensioner members 80 disposed above the topsheet 50. FIG. 3 provides a cross-sectional view that also depicts all five layers and their respective structural relationships. In an alternative embodiment, the inventive diaper may utilize a multipurpose material as one of the layers (which provides multiple functions). In this way, the number of layers that is required may be reduced, and, in some embodiments, a thinner diaper structure results.

Still referring to FIG. 2, the tensioner member or tensioner 80 is preferably a single piece elastic strip having an outside end edge 82a, an inside end edge 82b, and a pair of opposite side edges 82c. The tensioner 80 is disposed over the surface of the topsheet 50 such that the outside end edge 82a is secured adjacent (e.g., aligned with) the end edge 92 of the diaper 10 (i.e., at each of the front waist region 12 and the back waist region 14). In the embodiment of FIGS. 1–5, the tensioner 80 generally extends transversely between the ears 18, i.e., from adjacent one side edge 90 of the diaper 10 to adjacent the opposite side edge 90 (see FIG. 1). Along the longitudinal direction, the tensioner 80 extends inwardly from adjacent end edge 92 toward the crotch region 16 and just over the area of the core 46 (at an angle direction spaced from the core 46 and topsheet 50). Thus, the tensioner 80 occupies a substantial portion of the front waist region 12 or back waist region 14 except in the ear regions 18.

The tensioner 80 may be formed from elastic film, foam, a combination of nonwoven material and a stretchable film that is laminated together or a combination of two or more of these materials or laminate. The tensioner 80 may also be formed from a nonwoven material with elastic strands or elastic nonwoven material. In one suitable construction, the tensioner is formed primarily from an open cell polyurethane foam available from General Foam of Paramus, N.J. In yet another suitable construction, the tensioner is formed from an elastic apertured film available from Tredegar Industries of Cincinnati, Ohio.

The tensioner 80 is preferably comprised of at least three distinct sections: a fixed elasticized section 80a preferably secured adjacent one of the end edges 92 of the diaper 10, a fixed de-elasticized section 80b which extends inwardly (in the direction of the crotch area 16) from the elasticized section 80a, and an elasticized soffit section 80c which extends inwardly (in the direction of the crotch area 16) from the de-elasticized section 80b. In the flat, extended condition of the diaper, there is a vertical separation or vertical distance between the inside edge 80d of the soffit section 80c and the top surface of the core 46. Both the fixed elasticized section 80a and the fixed de-elasticized section 80b are secured (using any one of a number of securing means known in the art, e.g., by melting, sonic molding, or by applying adhesives) to a top surface of the topsheet 50.

Preferably, the tensioner 80 is secured to the top surface of the topsheet 50 while it (the tensioner 80) is disposed in the stretched condition and such that, when the secured tensioner 80 is subsequently released, the fixed elastic section 80a contracts with the adjacent portion of the front or back waist region 12, 14 intact. This forms a structure that provides the same functional advantages as a traditional waistband along the end edges 92 of the diaper 10. Accordingly, when the two end edges 92 are joined around the waist of the wearer, the two fixed elastic sections 80a are also joined and function generally as waistbands to secure the diaper 10 snugly around the waist of the wearer. Moreover, the two fixed elastic sections 80a form a quasi-seal around the waist of the wearer to prevent waste captured by the diaper 10 from leaking past the top or end edges 92.

The de-elasticized section 80b is formed with a plurality of voids or apertures 98 each of which functions to de-elasticize the immediate area adjacent the apertures 98. Collectively, the plurality of apertures 98 function to substantially de-elasticize the elastic material of the de-elasticized section 80b. The apertures 98 are typically created by slitting or cutting that section of the tensioner 80 at a stage in the manufacturing process before application of the tensioner 80 to the top sheet 50 or other subsurface layer. The size and number of apertures 80 are determined so as to prevent unnecessary weakening of the tensioner 80 and to guard against propagation of tears in the de-elasticized section 80b. Alternatively, de-elasticization is achieved by a heat deformation process which de-elasticizes the elastic material by applying heat on the targeted material before application of the tension 80 to the topsheet 50 or other subsurface layer. In other embodiments, de-elasticization is achieved by the addition of stiffening materials at the targeted area. In further embodiments, other methods of de-elasticization known to those skilled in the art are utilized. One advantage provided by the existence of a de-elasticized or non-elastic section is that the end strip can have elastic properties but the tendency of waist regions to contract (i.e., in the longitudinal direction) or crumple up is minimized.

It should be noted that the de-elasticized section 80b and the fixed section 80a are referred to herein as two sections of the tensioner 80 (e.g., a waist section of the tensioner 80) only for descriptive purposes. However, in the embodiment depicted in FIGS. 1–5, the fixed elastic section 80a and the fixed de-elasticized section 80b are formed from the same elastic material and differ only in that the de-elasticized section 80b has been applied and configured with the apertures 98. In alternative embodiments, these two sections may differ structurally and/or from a manufacturing standpoint.

Absent of voids or apertures, the soffit section 80c of the diaper 10 depicted in the drawings retains the strength and elasticity of the elastic material from which the tensioner 80 is formed. The soffit section 80c may also be referred to as the inward section of the tensioner 80. In FIGS. 1–5, the soffit section 80c is also formed from the same elastic material from which the fixed elastic section 80a and the fixed de-elasticized section 80b are formed. The soffit section 80c extends inwardly from the de-elasticized section 80b and upwardly (i.e., at an angle) away from the topsheet 50, to the extent that it is over a longitudinal edge portion 46a of the core 46.

In one aspect of the invention, substantially all of the central portion of the soffit section 80c is free from and is spaced from the top sheet 50, while the side portions or lateral edges of the soffit section 80c are secured to the top sheet 50 and the distal edges 36a of the leg gathers 36. As a result, the tensioner 80 functions to pull at least the intermediate portions of the side edges 90 or, more appropriately, the regions of the side edges (including the leg gathers 36) upwardly (by applying a contractile force across the waist region 16). These side edge regions are biased or brought to and maintained in an upstanding position along the crotch region 16 (see, e.g., FIGS. 3 and 4), to form upright side wall structures or side walls. As will be further explained below, these upstanding wide walls perform a containment or sealing function, as well as enhance the fit and comfort of the diaper 10.

As best shown in FIG. 1, the diaper 10 takes on an hourglass shape that is particularly advantageous to the fit and sealing ability of the diaper 10. This fit is further enhanced by the upstanding disposition of the leg gathers 36 (i.e., side walls) and the tension provided in the front and back waist regions 12, 14 by the tensioner 80. Another advantage provided by the inventive diaper design is that the hourglass shape of the diaper may be attained without having to cut leg openings into the composite web structure during the manufacturing process.

The combination of the upstanding side walls (including the leg gathers 36) and the elasticized soffit section 80c on both the front waist region 12 and the back waist region 14 of the diaper creates a retention compartment or containment pocket 96 at the crotch section region 16. This retention compartment 96 is generally deeper than conventional containment or central core areas. The upstanding leg gathers 36 or side edge regions serve as one set of retaining sidewalls for the retention compartment 96 while the oppositely-facing elasticized soffit sections 80c serve as retaining end walls of the retention compartment 96. The elasticized soffit sections 80c are, in one regard, particularly adapted to provide such a function because it extends upwardly and well above the core 46 (see e.g., FIG. 5). Thus, the retention compartment 96 may be referred to as having at least two elastic wall sections 80c and at least two intermediate wall sections 36 each disposed between elastic wall sections 80c. In alternative embodiments, the wall sections 36, 80c may be disposed in other areas of the article 10. The relatively deep retention compartment 96 of the present invention provides an improved structure and means for receiving and retaining body exudates in the central portion of the diaper 10. It should be noted, however, that the design of a deep retention compartment 96 is also applicable and advantageous in other disposable articles or garments 10.

In alternative embodiments of the present invention, the end strip may consist of more or less than three distinct sections. Further, the sections of the end strip may not be necessarily formed from the same material. Further yet, the end strip may be formed integrally as one piece with the topsheet or may include a portion of the topsheet. Additionally, the end strip may not necessarily be disposed adjacent the end edges and, in partially forming a containment wall of a retention compartment, may not necessarily be disposed in the front or back waist regions of the article. Some of these variations are discussed below. However, it should be noted that these variations or adaptations will be apparent to one skilled in the art upon reading the description and viewing the drawings provided herein.

In one alternative embodiment of the present invention, the tensioner consists of only the soffit section. Such a soffit section may be formed from an elastic material or a composition including an elastic material (e.g., elastic film or elastic strand(s)). The soffit section may be wholly elastic or include a portion having elastic properties. For example, the soffit may include a central portion that is formed from an elastic material (or otherwise elasticated), and side portions which are secured to the ends of leg gathers or portions of the side edges (so as to create upstanding side edge regions or side walls). Further, the soffit section may be formed by creating a fold with a portion of the topsheet and by elasticating at least a portion of the fold.

In yet another alternative embodiment, the disposable absorbent article according to the invention may include a traditional waistband structurally separate from the end strip and/or soffit section. Such a diaper may also include a non-elastic or de-elasticized section between the waistband and the soffit section. Further, such a non-elastic or de-elasticized section may be integrally formed with the soffit section.

In yet another embodiment, an end strip according to the invention is disposed on each lateral side of the core. Such an end strip includes an elastic or tensioned portion and may be formed, at least partially, with the topsheet and/or leg gathers. The end strip includes side portions which are secured to a side wall structure which may be formed from a folded portion of the topsheet, so as to bias the folded portion upwardly. Accordingly, a containment pocket of the disposable absorbent article is formed having a generally upwardly disposed and substantially continuous peripheral wall that is provided by the end strips and the side walls.

It should be further noted that, by locating an end strip at certain localized regions of the article as in the various embodiments described above, a tensioned or contracting zone is created in those regions. The tensioned zones provide one or more functions including providing a portion of a containment wall of a containment pocket. The tensioned zones may also function to bias generally upwardly a structure disposed adjacent each end of the tensioned zone such that the structures form side walls of the containment wall. In some embodiments, the tensioned zones also form a waistband portion.

Referring to FIGS. 3–5, the retention compartment 96 is characterized by a topsheet 50 (or portions thereof) that is raised or spaced, at least partially, above the core 46 to create storage compartments or storage spaces 150 therebetween. As will be shown below, the storage space 150 is particularly adapted to storage of fecal matter. The topsheet 50 is raised by attaching, to the topsheet 50, a plurality longitudinally extending elastic strands 102. The strands 102 form spaced apart ridges 152 in the topsheet 50, and valleys or depressions 154 between the ridges 152. Referring to the cross-section of FIG. 3, the valleys 154 are tacked down at bond points 106 (e.g., by adhesive or other mechanical means) to the acquisition layer 148). Referring to FIG. 4, slits or cutouts 104 are preferably provided in the valleys 154 of the topsheet 50 (i.e., in between the bond points 106).

As best shown in the cross-section of FIGS. 3–5, the retention compartment 96 or, more specifically, the topsheet 50 of the diaper 10, has an undulating profile formed by ridges 152 and valleys 154. The ridges 152 define inclined walls 146 which are directed downward to and terminate at the cutouts 104. As will be further explained below, the cutouts 104 serve as openings 104 for receiving bodily exudates into the storage space 150. In this regard, the configuration of the topsheet 50, particularly the provision of the inclined walls 146, help to direct the exudates into the openings 104. Preferably, the cutouts 104 are formed in the topsheet 50 prior to application of the topsheet 50 onto the composite web. It is also preferable to arrange the strands 102 (and thus the ridges 152 and the valleys 154) along the machine direction as shown in the Figures. Such an arrangement will facilitate the manufacturing process in general and, more specifically, facilitate the application of the elastic strands 102 onto the topsheet 50 and the composite web. The topsheet 50 preferably extends from the front waist region 12 into the back waist region 14. It is also preferable, but not necessary, to extend the elastic strands 102 from the front waist region 12 into the back waist region 14.

FIG. 4 is a lateral cross-section through the cutouts 104. This view illustrates the openings 104 in the topsheet 50 for receiving bodily exudates deposited on the topsheet 50. The topsheet configuration provides a funnel-like receptacle defined by the inclined walls 146 which facilitates the capture and direction of bodily exudates into the storage spaces 150. The acquisition layer 148 is provided between the topsheet 50 and the core 46 to capture the liquid portion of the exudates and to distribute or dissipate the liquids across the core 46. The solids portion of the exudates, however, are directed into the storage spaces 150. Although gravity provides the primary force which directs the exudates from the topsheet 50 into the storage spaces 150 and the core 46, the unique structure of the inventive diaper 10 facilitates and enhances this movement of the exudates.

In another aspect of the invention, the topsheet 50 is configured to provide a one-way valve structure in the form of the cutouts 104. More specifically, the arrangement of the topsheet 50 and the core 46 makes it difficult for solids directed into the storage spaces 150 from backing up or escaping outward and/or upward through the cutouts 104. As illustrated in the drawings, the bond points 106 keep the cutouts 104 or "valves" very close to the absorbent core 46 (or acquisition layer 148 if applicable); although, the elastic ridge strands 102 biases the topsheet 50 upwardly. Further, the lateral width of the openings 104 are substantially less than the lateral distance between the ridges 152 (although passing of the exudates below the topsheet 50 is facilitated by the inclined walls 146).

Accordingly, a retention compartment 96 of the present invention is provided having improved containment capabilities. The retention compartment 96 is characterized by a relatively deep compartment area for capturing body exudates. This deep containment area is defined by a unique continuous upstanding wall rising above the topsheet 50 and the core. The retention compartment 96 also features a unique structure for capturing the body exudates deposited into the crotch region and then storing the body exudates. This feature of the inventive diaper is embodied by a novel topsheet and core arrangement that directs the deposited body exudates into storage spaces below the topsheet. As a result, the inventive diaper provides a relatively larger containment capacity and a more effective means of storing and retaining the body exudates.

Figure 6:
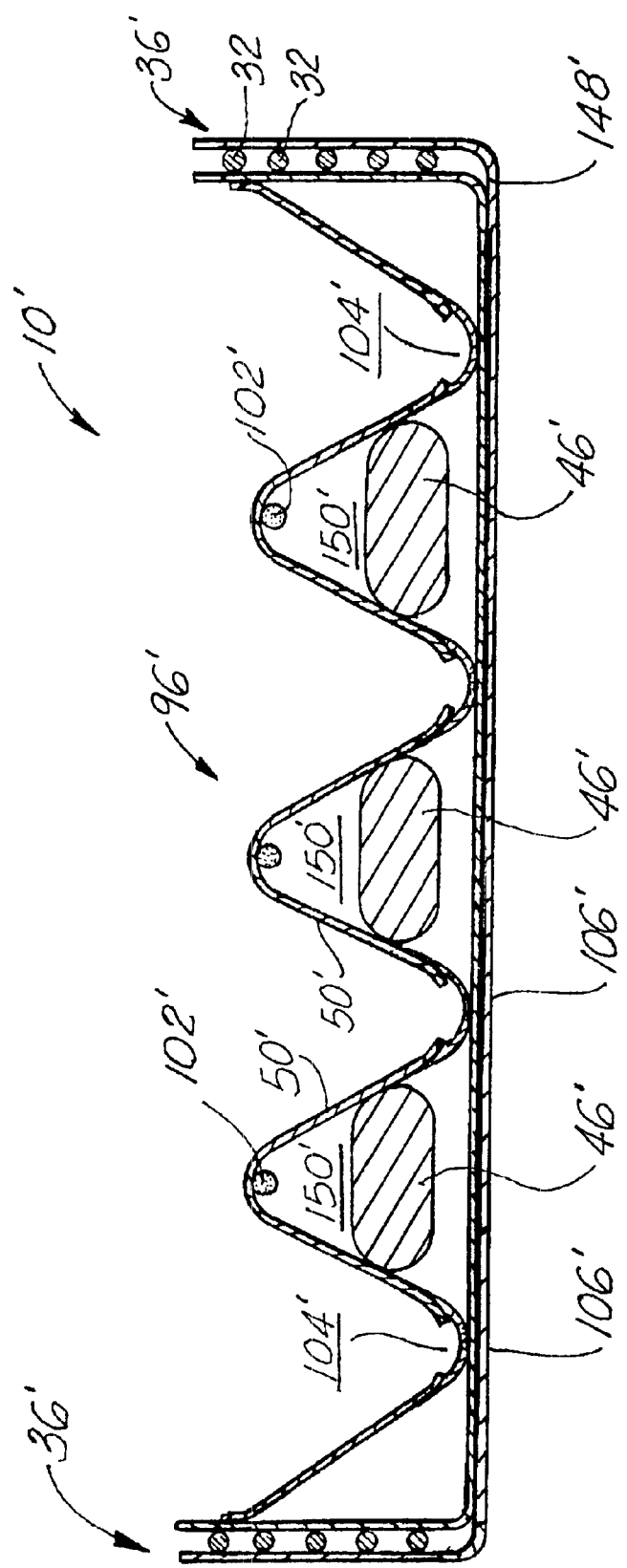
FIG. 6 is a cross-sectional view of an alternative embodiment of a disposable absorbent article according to the present invention.

FIG. 6 provides a cross-sectional view of an alternative disposable diaper 10' wherein a retention compartment 196' is provided with a plurality of substantially enclosed retention storage spaces 150'. In this particular embodiment, the storage spaces 150' are formed primarily below a series of segmented cores 46'. The segmented cores 46' are arranged longitudinally under the topsheet 50' and in between bond points 106'. Since the segmented cores 46' are not firmly secured to the topsheet 50' or to an acquisition layer 168', the segmented cores 46' are allowed to float upwards, i.e., when bodily exudates are received into the storage spaces 150'. In this particular embodiment, the solids portion of the exudates will tend to be driven, particularly via gravity, below the cores 46'. Accordingly, the storage spaces 150' of the retention compartment is provided primarily below the cores 46'.

Figure 7:
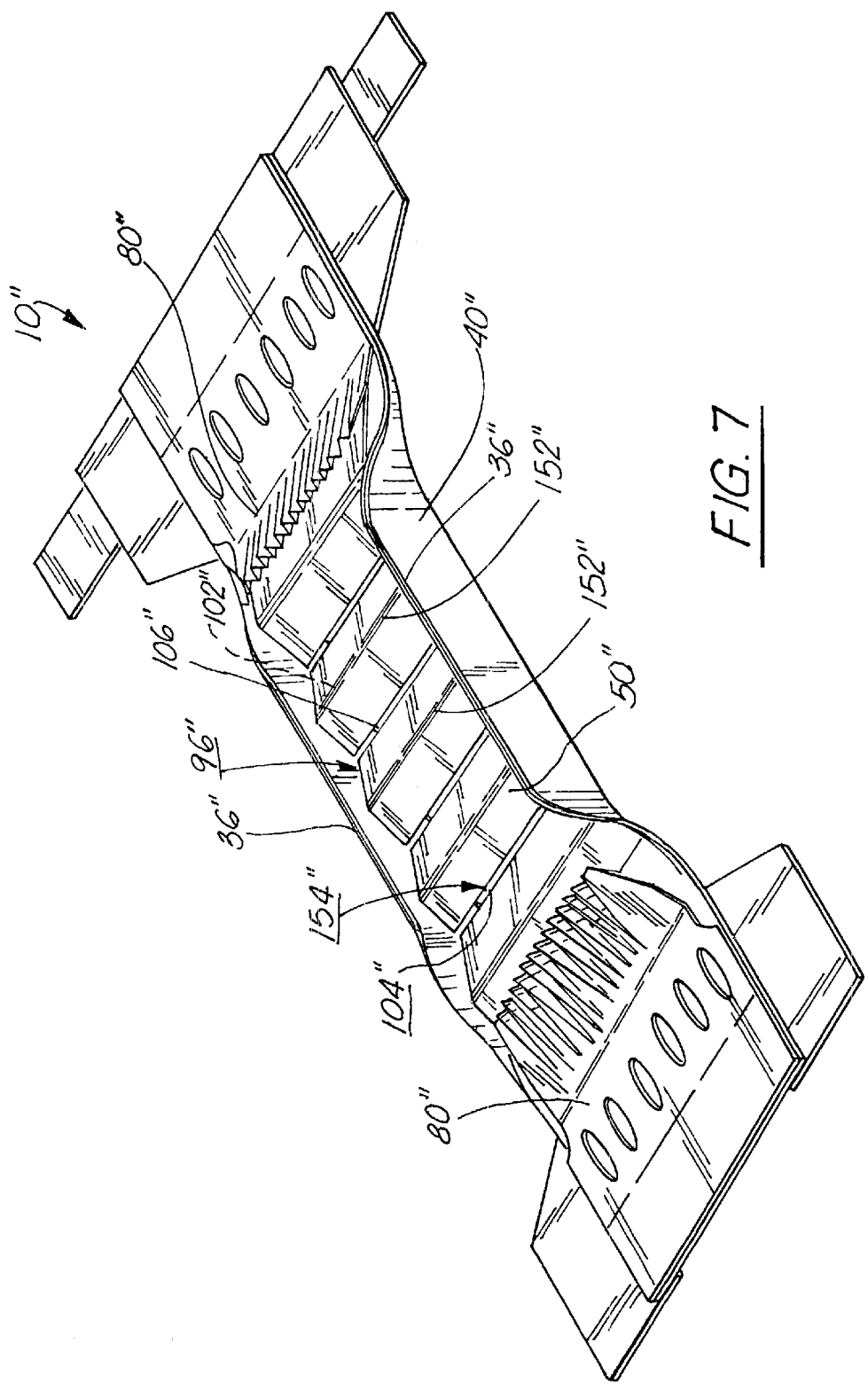
FIG. 7 is a perspective view of another alternative embodiment of a disposable absorbent article according to the invention.

FIG. 7 depicts yet another embodiment of the present invention, wherein a diaper 10" has a retention compartment 96" that is formed by a topsheet 50" having laterally disposed ridges 152" and valleys 154". More specifically, the topsheet 50" is provided with a plurality of laterally extending elastic strands 102", thereby creating a plurality of laterally extending ridges 152" and valleys 154". As with the embodiments of FIGS. 1–5 and FIG. 6, this particular embodiment is equipped with a plurality of bond points 106" for securing the topsheet 50" onto an acquisition layer 148" or other bottom layer. The diaper is also provided with cutouts 104" in between bond points 106" which serve as one-way valves for capturing and receiving bodily exudates deposited onto the retention compartment 96".

It should be noted that in the embodiments described above, the diaper does not necessarily have to be provided with the tensioners for the retention compartments or the storage spaces to function as intended. Moreover, the diaper does not have to conform to an hourglass shape as shown in the drawings although this diaper shape is preferred. It should also be noted that the topsheet does not necessarily have to extend onto the waist regions and edges of the diaper; the topsheet may be provided only over the core.

The following discussion expands upon the description of certain components described above which may be incorporated into a disposable absorbent article according to the invention:

Backsheet and Film Layer

A backsheet employed by a disposable absorbent article according to the invention may be constructed from a number of different suitable materials and, preferably, will have a breathable or vapor permeable attribute (distinguishing it from a liquid permeable material) such that air can pass therethrough. For example, the backsheet may be formed from a combination of a liquid permeable, nonwoven material and a film barrier that is laminated onto the nonwoven material. This type of backsheet design is in contrast to the design employed by any of the embodiments in FIGS. 1–7, wherein the backsheet 40 and the film barrier 42 are separate and distinct from one another. In either design, the film barrier may or may not be vapor permeable.

One construction suitable for incorporation with the design of the present invention, and more particularly, for the backsheet includes an outer layer of spunbond polypropylene fiber with a basis weight of about 14–25 grams per square meter (available from BBA Nonwovens, of Simpsonville, S.C.) and a polyethylene film of about 0.5 mil. (0.0005 inches) thickness adhesively laminated to the outer layer. Such a polyethylene film is available from, and manufactured by Tredegar Industries of Cincinnati, Ohio. This film may be laminated using adhesive available from National Starch and Chemical Company of Bridgewater, N.J. Yet another suitable construction for the backsheet includes a web of spunbond or SMS (spunbond/meltblown/spunbond) nonwoven material and a breathable or non-breathable film(s) of 0.5 mil. to 2.0 mil. thickness.

The backsheet covers at least the core 46, but preferably extends laterally beyond the core toward the side edges and the end edges of the article. The nonwoven portion of the backsheet may be provided only where the leg gathers turn upward, such that the section of the backsheet covering the core area is film.

Topsheet

The topsheet 50 may be constructed from any one of a wide range of liquid and vapor permeable hydrophilic materials. The topsheet may consist of or include nonwoven webs of natural fibers (e.g., wood or cotton) or synthetic fibers (e.g., polypropylene or polyester), a combination of such webs or fibers, or apertured film. One suitable topsheet material is a 15 gsm spunbond polypropylene from Avgol Nonwovens of Holon, Israel. In addition, the topsheet may be treated with a surfactant to facilitate liquid transfer, especially at a central zone or area of the topsheet located over the core and an inner surface of the topsheet may be treated with a chemical to increase the surface tension of liquids which pass through it.

In the embodiment of FIGS. 1–5, the topsheet 50 is formed from a single piece or sheet of material that covers substantially the entire area of the disposable absorbing article 10, including substantially all of the front waist region 12, back waist region 14, and crotch region 16. Further, the ear layer of the inner region 18 is formed from the same single topsheet material and, thus, may be referred to as being unitary with and forming lateral extensions of the topsheet material.

Alternatively, the topsheet may be formed from multiple different materials, which vary across the width of the topsheet. Such a multiple piece design allows for the creation of preferred properties in different zones of the topsheet. For example, the topsheet may comprise a center section above the absorbent core that is made of a hydrophilic material and a pair of leg cuff sections that are formed substantially from a hydrophobic material.

Absorbent Core

The absorbent core 46 of FIGS. 1–5 is generally centered about the longitudinal axis AA and lateral axis BB of the diaper 10, and is firmly secured between the topsheet 50 and the backsheet 40. The core 46 is preferably made from any one of several compositions (known in the art) which are adapted to absorb bodily liquids received through the topsheet 50. For example, the absorbent core may include a fluffed wood pulp component which provides wicking capability and structural integrity, and a high absorbency material (e.g., super absorbent) for containing liquids. The core may also include additional additives to provide other specific properties such as baking soda to provide improved odor absorbency. It should be noted, however, that the disposable absorbent article 10, according to the invention, is adapted to utilize absorbing cores of varying shapes and compositions.

Many absorbent cores known in the art are comprised of two components: a high absorbency material (or super absorbent material) and an absorbent composite. As expected, the majority of the volume of such an article (i.e., bulkiness) is due to the composite. The high absorbency material may be one of numerous compounds. A suitable material may include inorganic materials such as polyvinyl alcohol, polyacrylates, various grafted starches, and cross linked polysodiumacrylate. Further, the high absorbency material may be manufactured and utilized in the diaper in numerous forms including, but not limited to, particles, fibers, foams, and layers. On the other hand, the absorbent composite is generally a composite material such as a defiberized fiber, or a wood pulp.

Another relatively new material for core composition is the "MicroThin Absorbent Composite" under the "Mega-Thin" brand name. This material has been developed by Japan Absorbent Technology Institute of Japan. The material is a composite of SAP (superabsorbent polymer), MFC (microfibrillated cellulose) and nonwoven which is characterized by its lighteners, thinners and softeners. See PCT Application PCT/JP97/04606, which is hereby incorporated by reference).

An application of any such material to the present structure according to the invention will be apparent to a person skilled in the art. In addition, the specific structural configuration of the disposable absorbent article of the invention may also be manipulated to enhance absorbency (e.g., channels or grooves may be created to ultimately disperse liquid waste received in the deep containment).

Optional Layers

The disposable absorbent article according to the invention may contain additional layers including an acquisition layer or surge layer, preferably situated between the topsheet and the core. One function of such an acquisition layer is to spread out or disperse liquid flow so that liquid is distributed more evenly over the core surface. This serves to slow down the flow so that the liquid has adequate time to be absorbed by the core. The acquisition layer also serves to prevent the core from being saturated locally, while a substantial remainder of the core is not absorbing any liquid.

Tape Tabs

The article must be secured to the wearer. This is most important with respect to diapers since they are not pulled upon the wearer, like training pants, or incontinent briefs, but are fastened around the wearer. The securing elements compliment the elastic members by effecting a quasi-seal between the wearer and the waist band and leg cuffs, so that liquid is contained within the article which is then absorbed; in other words, so that it does not leak through gaps between the wearer and the edge of the article. The securing elements may be adhesive, mechanical fasteners hook and loop features, or conceivably strings, i.e., anything that will secure one end of the article to the longitudinally opposite end.

In the adhesive devices employed by the diapers in FIGS. 1–7, the article 10 is affixed to the wearer by tape fasteners 26 permanently affixed to (e.g., sewn directly into) the backsheet 40. The tape fasteners 26 are contacted with the transversely opposite ear 22 extending from the backsheet where they remain affixed due to an adhesive compound applied to the fasteners 26.

The present inventive design of a disposable absorbent article is well adapted to carry out the diaper or other objects and attain the ends and advantages previously mentioned, as well as others in that area. While description of a particular disposable diaper has been given for the purpose of disclosure, numerous changes in the details of construction of the diaper or other disposable absorbent article, in the arrangement of its part and in the steps of the process of manufacturing the article may be made. These changes will readily suggest themselves to those skilled in the art and are encompassed within the spirit of the invention and the scope of the appended claims.

What is claimed is:

1. A disposable absorbent article having a front waist region, a back waist region, and a crotch region located between said front and back waist regions, said article comprising:

a backsheet;

a plurality of absorbent cores, said cores being generally spaced apart from one another and disposed above said backsheet and generally in said crotch region; and a topsheet disposed above said plurality of absorbent cores, said topsheet being equipped with a plurality of spaced apart elastic strands which are attached thereto to form a plurality of spaced apart ridges, wherein said strands are adapted to bias said topsheet upwardly and wherein portions of said topsheet located between said strands are tacked down to form depressions between said ridges; and wherein said topsheet is further equipped with a plurality of openings located between said ridges, said openings being adapted to direct bodily exudates received in said crotch region toward said cores;

wherein said topsheet is tacked down at locations between said cores and at least a number of said openings are generally located between said cores;

wherein said storage space is generally located below said cores, said storage space being generally adapted for storage of a solids portion of said bodily exudates; and wherein said topsheet includes generally inclined walls directed downwardly from said ridges to said openings.

2. The article of claim 1, wherein each of said openings has a lateral width substantially less than the lateral distance between said ridges.

3. A disposable absorbent article having a front waist region, a back waist region, and a crotch region located between said front and back waist regions, said article comprising:

a backsheet;

a plurality of absorbent cores disposed above said backsheet and generally in said crotch region, said cores being generally spaced apart from one another; and a topsheet disposed above said absorbent core, said topsheet being equipped with a plurality of spaced apart elastic strands which are attached thereto to form a plurality of spaced apart ridges, wherein said strands are adapted to bias said top sheet upwardly and wherein portions of said topsheet located between said strands are tacked down to form depressions between said ridges; and wherein said topsheet is further equipped with a plurality of openings located between said ridges, said openings being adapted to direct bodily exudates received in said crotch region toward said core;

wherein said topsheet is tacked down at locations between said cores and each of said openings is generally located between said cores; and wherein storage space is generally located below each of said cores, said storage space being generally adapted for storage of the solids portion of said bodily exudates.

4. The article of claim 3, wherein said topsheet includes generally inclined side walls directed downwardly from said ridges to said openings.

5. The article of claims 3, wherein each of said openings has a lateral width substantially less than the lateral distance between said ridges.

* * * * *